(12) United States Patent
Malinovskaya et al.

(10) Patent No.: US 7,847,933 B2
(45) Date of Patent: Dec. 7, 2010

(54) CARS MICROSCOPY AND SPECTROSCOPY USING ULTRAFAST CHIRPED PULSES

(75) Inventors: Svetlana Malinovskaya, Clifton, NJ (US); Vladimir Malinovsky, Clifton, NJ (US)

(73) Assignee: Stevens Institute of Technology, Hoboken, NJ (US)

( * ) Notice: Subject to any disclaimer, the term of this patent is extended or adjusted under 35 U.S.C. 154(b) by 280 days.

(21) Appl. No.: 12/154,231

(22) Filed: May 21, 2008

(65) Prior Publication Data

US 2008/0291443 A1 Nov. 27, 2008

Related U.S. Application Data

(60) Provisional application No. 60/931,176, filed on May 22, 2007.

(51) Int. Cl.
*G01J 3/44* (2006.01)
(52) U.S. Cl. ..................................................... 356/301
(58) Field of Classification Search ................. 356/301
See application file for complete search history.

(56) References Cited

U.S. PATENT DOCUMENTS

2005/0168735 A1*  8/2005  Boppart et al. .............. 356/301

OTHER PUBLICATIONS

S. A. Malinovskaya, Phys. Rev. A 73, 033416 (2006).
T. Hellerer, A. M. K. Enejder, and A. Zumbusch, Appl. Phys. Lett. 85, 25 (2004).
G. W. H. Wurpel, J. M. Schins, and M. Muller, Opt. Lett. 27, 1093 (2002).
E. M. Vartiainen, H. A. Rinia, M. Muller, and M. Bonn, Optics Express 14, 3622 (2006).
K. P. Knutsen, B. M. Messer, R. M. Onorato and R. J. Saykally, J. Phys. Chem. B 110, 5854 (2006).
A. Zumbusch, G. Haltom, X. S. Xie, Phys. Rev. Lett. 92, 4142 (1999).
E. O. Potma. X. S. Xie, Optics & Photonics News (November), 40 (2004).
C. L. Evans, E. O. Potma, M. Puorishaag, D. Cote, C. P. Lin, X. S. Xie, Proc. Natl. Acad. Sci. 102, 16807 (2005).
N. Dudovich, D. Oron, Y. Silberberg, Nature 418, 512 (2002).
B. Yellampalle, R. D. Averitt, A. Efimov, A. J. Taylor, Optics Express 13, 7672 (2005).
Ogilvie, D. Debarre, X. Solinas, J. Martin, E. Beaurepaire, M. Joffre, Optics Express 14, 759 (2006).
E. Gershgoren, R. A. Bartels, J. T. Fourkas, R. Tobey, M. M. Mumane and H. C. Kapteyn, Opt. Lett. 28, 361 (2003).
K. P. Knutsen, J. C. Johnson, A. E. Miller, P. B. Petersen and R. J. Saykally, Chem. Phys. Lett. 387, 436 (2004).

* cited by examiner

*Primary Examiner*—Tarifur Chowdhury
*Assistant Examiner*—Abdullahi Nur
(74) *Attorney, Agent, or Firm*—Opticus IP Law PLLC

(57) ABSTRACT

Linear chirped pulses in a Raman excitation scheme provide selective excitation of only one target transition (single mode) in a molecule without disturbing any other transitions or molecules. Selectivity is guaranteed by the adiabaticity of the pulse excitation, which allows manipulation by only a resonant mode while leaving all of the other modes unperturbed. This in turn allows for enhanced imaging or spectroscopic analysis of a sample that contains one or more of the molecules.

18 Claims, 9 Drawing Sheets

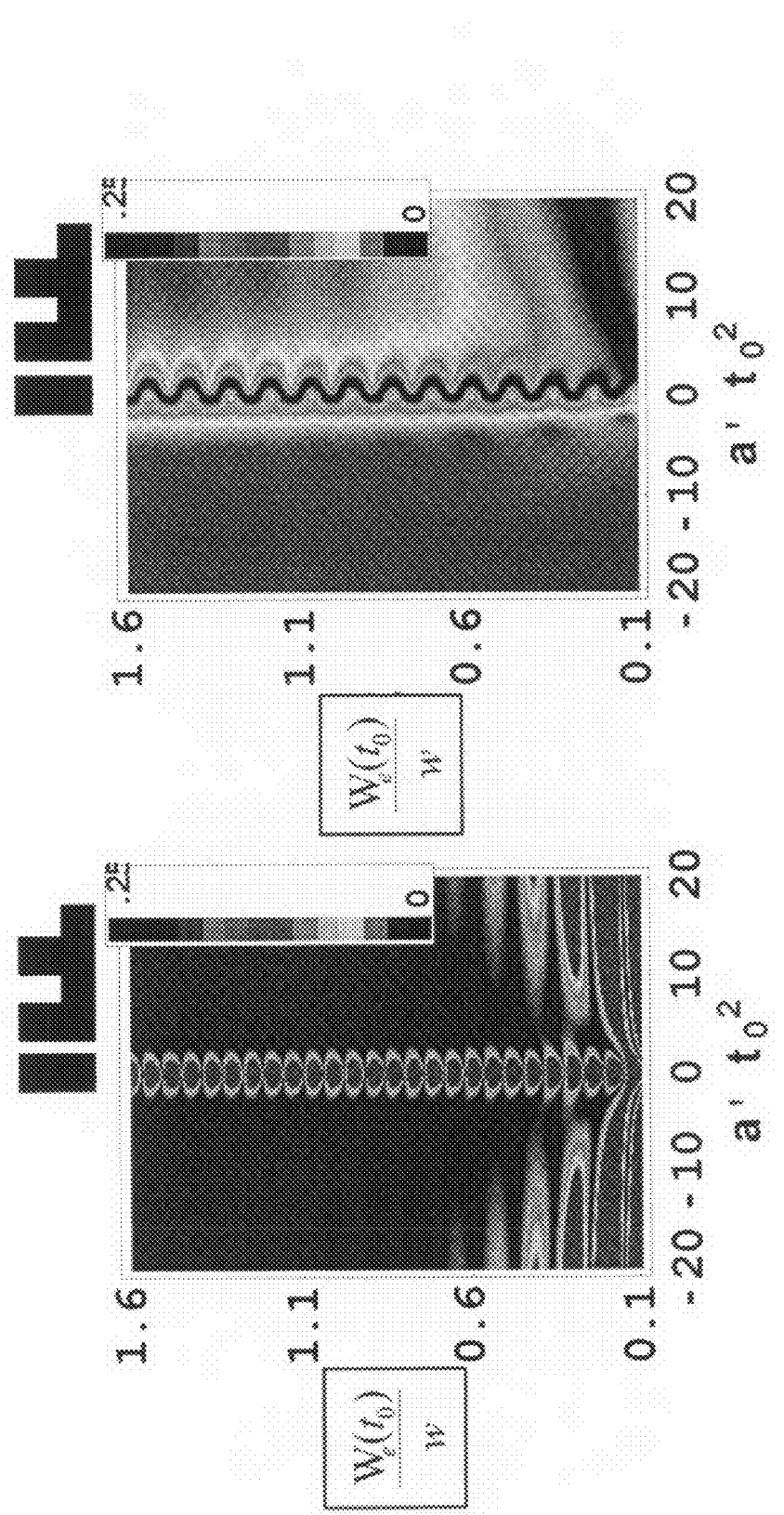

CARS MICROSCOPY AND SPECTROSCOPY USING ULTRAFAST CHIRPED PULSES

CLAIM OF PRIORITY

This application claims the benefit of priority under 35 U.S.C. §119(e) of U.S. Provisional Application Ser. No. 60/931,176, entitled "CARS microscopy and spectroscopy using ultrafast chirped pulses" filed on May 22, 2007, which application is incorporated by reference herein.

FIELD OF THE INVENTION

The present invention relates to coherent anti-Stokes Raman scattering (CARS) and the application of same to ultrafast microscopy, coherent spectroscopy and imaging.

BACKGROUND OF THE INVENTION

Ultrashort laser pulses have been widely used in basic studies for several decades. Recently there has been interest in developing methods of nonlinear coherent microscopy for chemically-selective imaging of biological systems. In recent years, coherent anti-Stokes Raman scattering (CARS) has attracted a lot of attention since it allows one to receive chemically selective vibrational information and has several advantages in comparison with fluorescent and spontaneous Raman scattering based methods.

CARS is a third order nonlinear optical process involving three laser beams: pump, Stokes and probe beams with frequencies $\omega_p$, $\omega_s$ and $\omega_{pr}$, respectively, as reflected in the energy level diagram of FIG. 1. These three beams interact with a sample and generate an anti-Stokes field with frequency $\omega_{as}=\omega_p+\omega_{pr}-\omega_s$ higher than any excitation frequencies. CARS can therefore be detected in the presence of photon-induced fluorescence. Because CARS is a coherent process, the CARS signal is much larger than the spontaneous Raman scattering signal and, in addition, it has spatial (directional) selectivity defined by a phase-matching condition. The phase-matching condition requires the sum of wave vectors of incoming waves (pump and probe) to be equal to sum of wave vectors of outgoing waves (Stokes and anti-Stokes), which means that the laser beams have to be properly aligned.

When the phase-matching condition is satisfied, one has to address a second important aspect of CARS microscopy—namely, designing pulses that provide the maximum coherence on the particular vibrational transition of the target molecule(s) in the sample being analyzed.

SUMMARY OF THE INVENTION

An aspect of the invention is a method that uses pulse shaping techniques that allow for selective excitation of select molecules of a sample in order to generate a signal that can then be processed to perform CARS microscopy or CARS spectroscopy of the sample.

In one aspect of the invention, linear chirped pulses in a Raman excitation scheme provide selective excitation of only one target transition (i.e., a single mode) in a molecule in a sample (e.g., biological sample) without disturbing any other transitions or molecules. Selectivity is guaranteed by the adiabaticity of the pulse excitation, which allows manipulation by only a resonant mode while leaving all of the other modes unperturbed. This in turn allows for enhanced imaging or spectroscopic analysis of a sample that contains different molecules.

In another aspect of the invention, intense femtosecond pulses are used to perform CARS imaging. The large bandwidth of the pulse provides the flexibility necessary to manipulate by frequency components and to apply a time-dependent phase on the pulse. The high intensity of the femtosecond laser pulses provides enough power to maintain the high Rabi frequencies necessary for adiabatic evolution of rovibrational (i.e., coupled rotational and vibrational) states.

Another aspect of the invention involves performing CARS microscopy by providing a sequence of two linearly chirped pulses (pump and Stokes pulses) to a sample to be measured or otherwise analyzed (e.g., imaged), wherein the central frequencies of the pulses are off-resonant to the corresponding single-photon transitions, but are arranged to be in two-photon Raman resonance with the frequency of a target transition. The pulse envelopes are chosen so that pump and Stokes Rabi frequencies are completely overlapped, wherein one of the pulses (pump or Stokes) is linearly chirped (positive or negative), while other pulse (Stokes or pump) is linearly chirped with a roof shape—that is to say, it is chirped in the opposite direction (negative or positive) until the center time when the instantaneous frequency difference between the pump and Stokes pulses reaches the resonance frequency of the target vibrational transition. It then changes the sign of the chirp (positive or negative). Values of the intensities and chirp rates of the pulses are chosen to satisfy an adiabaticity criterion. This combination of laser pulses creates maximum coherence of the target transition without excitation of other transitions in the sample. This in turn leads to an enhanced signal from the sample (e.g., a biological sample such as animal tissue or cells) that is then analyzed (e.g., imaged) to deduce one or more properties of the sample.

The pulse sequences of the present invention can be used for CARS microscopy or spectroscopy to analyze various types of samples, and in particular biological samples.

BRIEF DESCRIPTION OF THE DRAWINGS

FIGS. 4A and 4B are density plots of coherence in the resonant (FIG. 4A) and off-resonant (FIG. 4B) system;

DETAILED DESCRIPTION OF THE INVENTION

I. Theoretical Background

Figure 1:
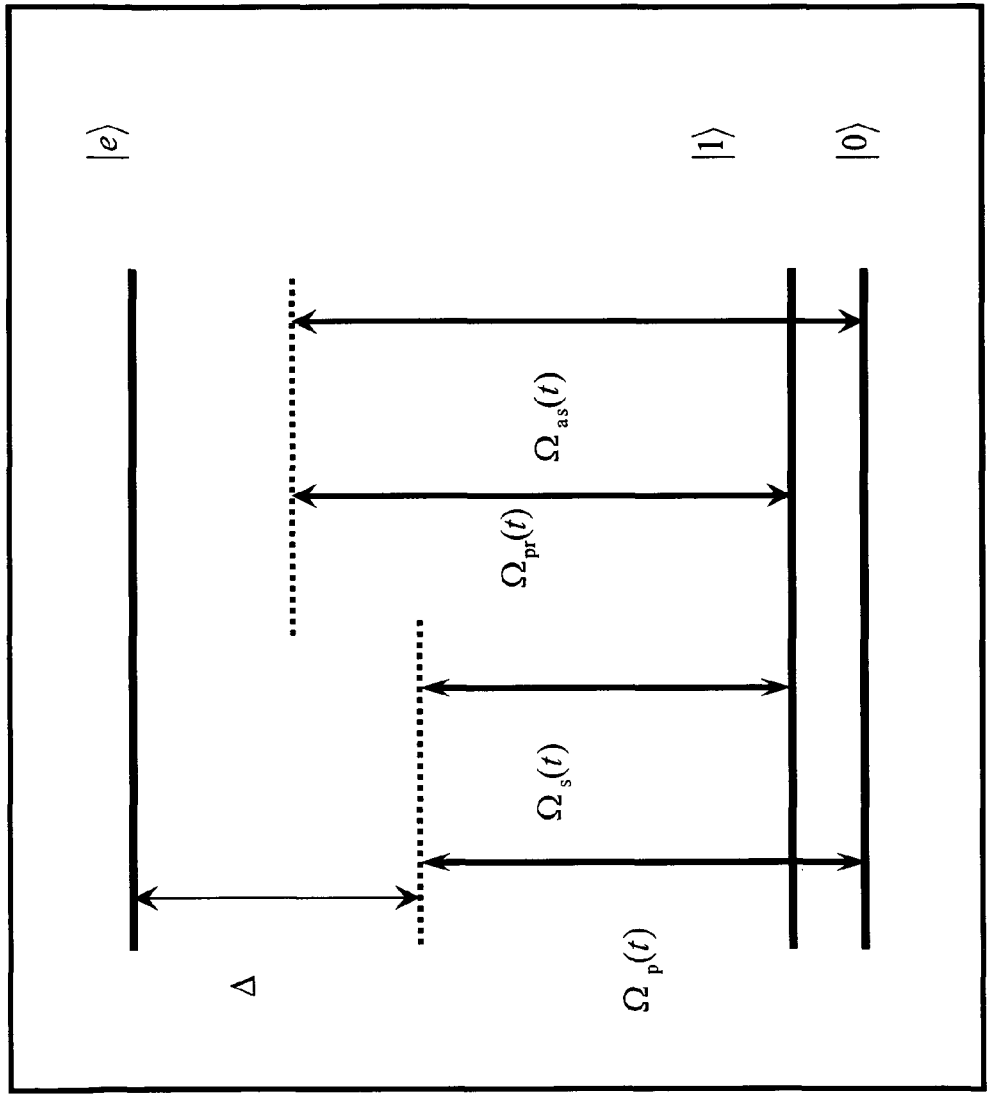
FIG. 1 is an energy level diagram for CARS illustrating the pump, Stokes, probe and anti-Stokes transitions.
Figure 2:
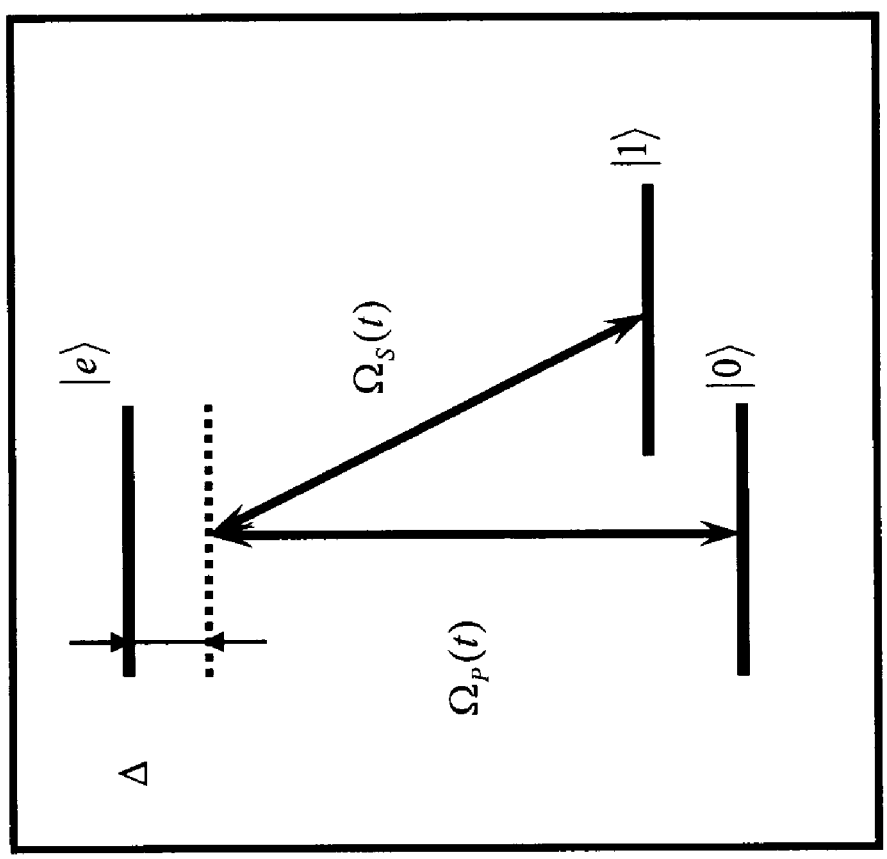
FIG. 2 is an energy level diagram of a three-level system representative of a molecule in a sample to be analyzed according to the CARS-based systems and methods of the present invention.

Consider a three-level $\Lambda$ system such as shown in FIG. 2, with two rovibrational states $|0\rangle$ and $|1\rangle$ with energy $\epsilon_0$ and $\epsilon_1$ correspondingly and an excited state $|e\rangle$ with the energy $\epsilon_e$. To manipulate (in time) the total wave function of the quantum system $$|\psi(t)\rangle = a_0(t)|0\rangle + a_1(t)|1\rangle + b(t)|e\rangle, \tag{1.1}$$

where $a_{0,1}(t)$ and $b(t)$ are the probability amplitudes to be in state $|0\rangle$ or $|1\rangle$, we use external fields which in general can be described as $$E_{1,2}(t) = E_{1,2}^{(0)}(t)\cos\phi_{1,2}(t), \tag{1.2}$$

where $E_{1,2}^{(0)}(t)$ are the field envelopes and $\phi_{1,2}(t)$ are the time-dependent phases. We are considering here a case of liner chirp so that $$\phi_{1,2}(t) = \phi_{1,2}^{(0)} + \omega_{1,2}^{(0)} t + \alpha_{1,2}\frac{t^2}{2}, \tag{1.3}$$

where $\phi_{1,2}^{(0)}$ are the initial phases, $\omega_{1,2}^{(0)}$ are is the center frequencies, and $\alpha_{1,2}$ are the chirps of the pulses.

Here we use the time-dependent pump and Stokes field envelopes of the Gaussian form $$E_{1,2}^{(0)}(t) = E_{1,2}^{(0)} \exp\left[-\frac{t^2}{2\tau^2}\right], \tag{1.4}$$

with the chirp-dependent pulse duration $\tau$, and where $E_{1,2}^{(0)}$ are the respective peak pulse amplitudes. We assume that the chirp is applied to the pulse using conventional linear optics, that is, by using a grating or prism pair for example. Therefore, chirping a pulse preserves the band-width and the pulse energy.

Applying these requirements and using Fourier transformation one can obtain the following relations between pulse parameters (see, V. S. Malinovsky and J. L. Krause, "General theory of population transfer by adiabatic rapid passage with intense, chirped laser pulses", *Eur. Phys. J. D*, V. 14, P. 147-155 (2001), which publication is incorporated by reference herein)

$$\tau = \tau_0\sqrt{1 + \alpha'^2/\tau_0^4}, \tag{1.5}$$

where $\tau_0$ is the transform-limited pulse duration, and $\alpha'$ is the spectral chirp;

$$I = I_0 \frac{1}{\sqrt{1 + \alpha'^2/\tau_0^4}}, \tag{1.6}$$

where $I_0 = (E_i^{(0)})^2$ is the peak intensity of the transform-limited pulse. Chirps in time domain, $\alpha$, and in frequency domain, $\alpha'$, are related by the equation $$\alpha = \frac{\alpha'/\tau_0^4}{1 + \alpha'^2/\tau_0^4}. \tag{1.7}$$

The relations (1.5)-(1.7) are valid for both pump and Stokes fields.

Now we consider the interaction of the pulses with the three-level system of FIG. 2. In the field interaction representation, after assuming the rotating wave approximation, we obtain the Schrödinger equation $$i\begin{pmatrix} \dot{a}_0(t) \\ \dot{a}_1(t) \\ \dot{b}(t) \end{pmatrix} = \frac{1}{2}\begin{pmatrix} 2\alpha_1 t & 0 & -\Omega_{p0} \\ 0 & 2(\delta + \alpha_2 t) & -\Omega_{s0} \\ -\Omega_{p0}(t) & -\Omega_{s0}(t) & 2\Delta \end{pmatrix}\begin{pmatrix} a_0(t) \\ a_1(t) \\ b(t) \end{pmatrix}, \tag{1.8}$$

where $\Omega_{p0}(t)$, $\Omega_{s0}(t)$ are the Rabi frequencies, and $\delta$ is the two-photon detuning. Assuming large single photon detuning of the field frequencies from the transition frequencies to the $|e\rangle$ state we make adiabatic elimination of the $b(t)$ amplitude and finally obtain:

$$i\begin{pmatrix} \dot{a}_0(t) \\ \dot{a}_1(t) \end{pmatrix} = \tag{1.9}$$

$$\left\{-\frac{1}{2}\left(\delta + (\alpha_2 - \alpha_1)t + \frac{\Omega_{p0}^2(t) - \Omega_{s0}^2(t)}{4\Delta}\right)\hat{\sigma}_z - \Omega_e(t)\hat{\sigma}_x\right\}\begin{pmatrix} a_0(t) \\ a_1(t) \end{pmatrix},$$

where $\Omega_e(t) = \Omega_{p0}(t)\Omega_{s0}(t)/(4\Delta)$ is the effective Rabi frequency, and $\hat{\sigma}_{z,x}$ are the Pauli matrices.

According to Eq. (1.9) it is clear that the excitation scheme can be simplified by choosing identical time-dependent Rabi frequencies $\Omega_{p0}(t) = \Omega_{s0}(t)$, which removes the influence of the ac Stark shifts on the system dynamics. Thus we obtain $$i\begin{pmatrix} \dot{a}_0(t) \\ \dot{a}_1(t) \end{pmatrix} = \left\{-\frac{1}{2}(\delta + (\alpha_2 - \alpha_1)t)\hat{\sigma}_z - \Omega_e(t)\hat{\sigma}_x\right\}\begin{pmatrix} a_0(t) \\ a_1(t) \end{pmatrix}. \tag{1.10}$$

The diagonal elements of the Hamiltonian in Eq. (1.10) describe bare state energies in the field interaction representation. They depend on the chirp parameters $\alpha_{1,2}$ and also on the detuning $\delta$. Notably, there is no dependence of the diagonal elements on the ac Stark shifts caused by the pump and Stokes fields, in contrast to the method described in T. Hellerer, A. M. K. Enejder, and A. Zumbusch, "Spectral focusing: High spectral resolution spectroscopy with broadband laser pulses", Appl. Phys. Lett., 85, 25 (2004). Because the diagonal elements have the same magnitude, they cancel each other. The off-diagonal elements describe coupling of the bare states through the effective Rabi frequency $\Omega_e(t)$, which is also a function of the chirp rate.

Figure 3A:
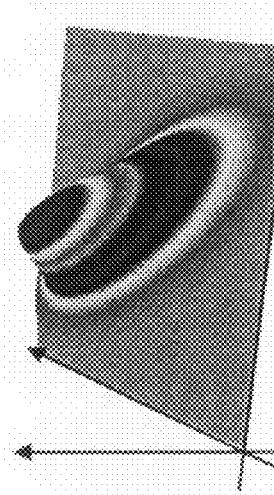
FIGS. 3A and 3C are Wigner plots of the pump and Stokes pulses.
Figure 3B:
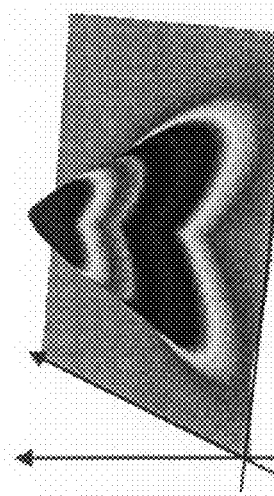
FIGS. 3B and 3D are the corresponding contour plots (projections) for FIGS. 3A and 3C.
Figure 3C:
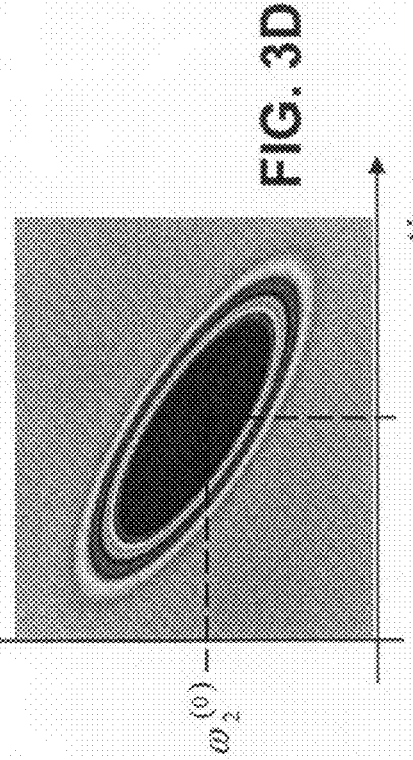
Figure 3D:
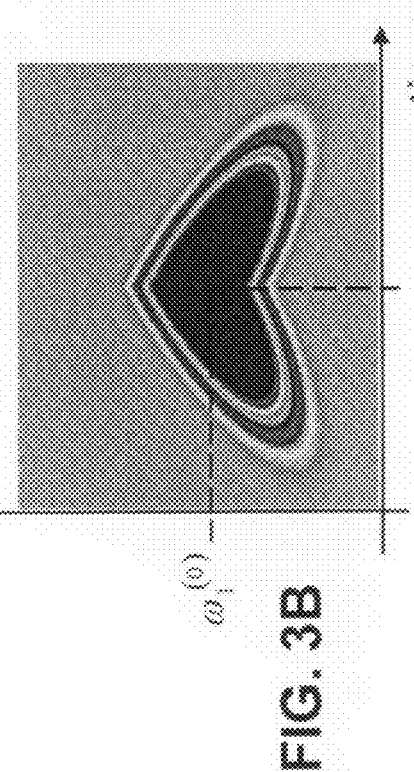

The proposed method assumes $\alpha_2$ to be constant, giving a monotonous change of the Stokes pulse frequency, and assumes $\alpha_1$ to have the same magnitude and opposite sign before the central time to (when the field amplitude reaches maximum, above it is chosen $t_0=0$) and then flips sign (see FIGS. 3A-3D). At $t_0$ the difference between the pump and Stokes pulse frequencies comes into resonance with the $|1\rangle \leftrightarrow |2\rangle$ system frequency and stays in resonance for the rest of the time. This method is called the "roof method" in accordance with the temporal shape of the pump pulse instantaneous frequency (FIGS. 3A and 3B).

The roof method induces qualitatively different dynamics in the resonant and off-resonant two-level systems exposed to the pump and Stokes laser fields. The adiabatic passage takes place in this case and leads to the maximum coherence in the resonant ($|1\rangle \leftrightarrow |2\rangle$) two-level system as illustrated in FIG. 4A, and minimum coherence in the off-resonant ($|3\rangle \leftrightarrow |4\rangle$) two-level system as illustrated in FIG. 4B in the broad range of peak intensities. In fact, the upper limit for the intensity is defined by the safety of the sample being measured.

The adiabaticity of the dynamics may be well understood from the consideration of the dressed state picture. Using the standard procedure of diagonalization of the Hamiltonian in Eq. (1.10) one has the dressed state energies $$\lambda_{\mp} = \mp \frac{1}{2} \sqrt{\Lambda^2(t) + 4\Omega_e^2(t)} \quad (1.11)$$

where $\Lambda(t) = \delta + (\alpha_2 - \alpha_1)t$. The Corresponding transformation matrix is $$\hat{R}(t) = \frac{1}{2} \begin{pmatrix} \sqrt{1 + \frac{\Lambda(t)}{\sqrt{\Lambda^2(t)+4\Omega_e^2(t)}}} & \sqrt{1 - \frac{\Lambda(t)}{\sqrt{\Lambda^2(t)+4\Omega_e^2(t)}}} \\ -\sqrt{1 - \frac{\delta}{\sqrt{\Lambda^2(t)+4\Omega_e^2(t)}}} & \sqrt{1 + \frac{\Lambda(t)}{\sqrt{\Lambda^2(t)+4\Omega_e^2(t)}}} \end{pmatrix}. \quad (1.12)$$

Using Eqs. (1.11)-(1.12) we find that in the adiabatic approximation of the evolution operator is:

$$\hat{U}(t) = \frac{1}{\sqrt{2}} \quad (1.13)$$

$$\begin{pmatrix} e^{i\xi(t)}\sqrt{1 + \frac{\Lambda(t)}{\sqrt{\Lambda^2(t)+4\Omega_e^2(t)}}} & e^{-i\xi(t)}\sqrt{1 - \frac{\Lambda(t)}{\sqrt{\Lambda^2(t)+4\Omega_e^2(t)}}} \\ e^{i\xi(t)}\sqrt{1 - \frac{\Lambda(t)}{\sqrt{\Lambda^2(t)+4\Omega_e^2(t)}}} & e^{-i\xi(t)}\sqrt{1 + \frac{\Lambda(t)}{\sqrt{\Lambda^2(t)+4\Omega_e^2(t)}}} \end{pmatrix},$$

where $$\xi(t) = \frac{1}{2} \int_{-\infty}^{t} \sqrt{\Lambda^2(t') + 4\Omega_e^2(t')} \, dt'$$

is the effective pulse area. It is clear from Eq. (1.13) that if initially the ground is populated, $\alpha_0(-\infty)=1$, and the chirped pulses are applied as discussed above (so that at a final time $\Lambda(t \to \infty)=0$) one obtains for the resonant case, $\delta=0$, $$a_0(\infty) = a_1(\infty) = \frac{1}{\sqrt{2}} e^{i\xi(\infty)}, \quad (1.14)$$

which gives a maximum coherence $\rho_{10} = \alpha_0(\infty)\alpha_1^*(\infty) = \frac{1}{2}$.

For the off-resonant case, $\delta \neq 0$, the situation is more complicated. The population of the states at a final time depends on sign of the detuning, $\delta$, and the chirps. Qualitatively, the results can be understood from analysis of the dressed state picture: non-zero two-photon detuning effectively shifts the crossing time between the bare-state energies $\lambda_-$ and $\lambda_+$ with respect to the central time, $t_0$, when the effective Rabi frequency has maximum value. If the crossing takes place before $t_0$ and the effective Rabi frequency is large enough so that $\Omega_e^2(t)/(2|\alpha|) > 1$ then whole population is transferred to the excited vibrational state. If the effective Rabi frequency is small so that $\Omega_e^2(t)/(2|\alpha|) < 1$ then the whole population remains in the ground vibrational state. In either case, the coherence at the final time is zero. The time delay (difference) between $t_0$ and crossing time is defined by $\delta/(2\alpha)$. Therefore, if $\delta/(2\alpha)$ is positive, then the crossing does not occur at all and there is no population transfer so that the coherence is zero.

To obtain robust adiabatic pulse parameters, in an example embodiment the initial transform-limited pulses have to be stretched by chirping by about 10 times or more—e.g., a 100 fs (femtosecond) pulse has to be stretched to several picoseconds.

II. Apparatus

Figure 5:
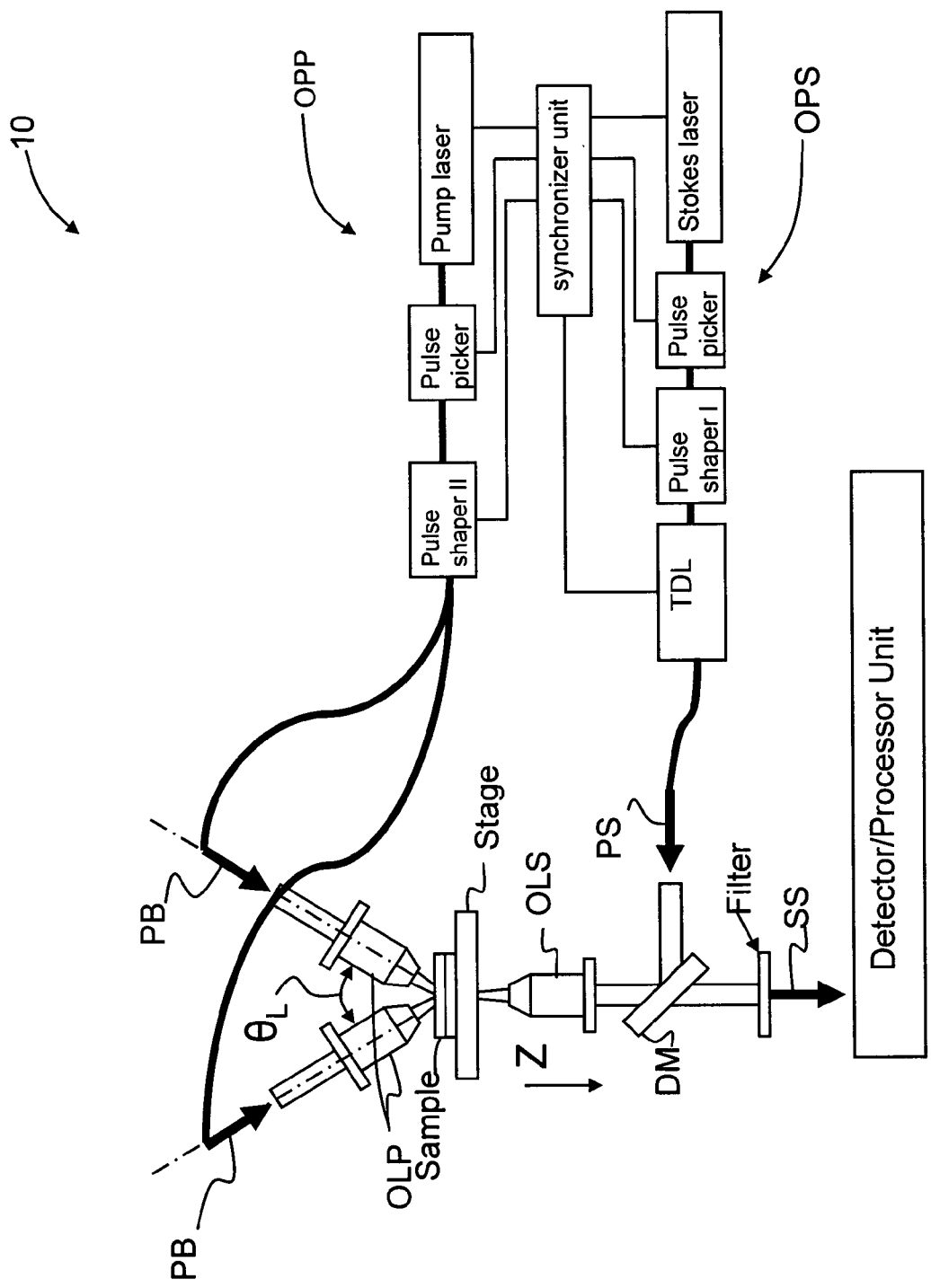
FIG. 5 is a schematic diagram of an example embodiment of a CARS apparatus of the present invention used for performing CARS microscopy or CARS spectroscopy.

The present invention includes methods of and apparatus for performing microscopic imaging and performing spectroscopy using ultrafast, strong laser pulses. A schematic diagram of an example embodiment of a CARS imaging system 10 according to the present invention is shown in FIG. 5. The apparatus includes two synchronized lasers (pump and Stokes) used to create maximum coherence on a predetermined molecular vibrational transition ("target transition") in a sample.

Each laser system generates a corresponding train of pump pulses PP and Stokes pulses PS that travel over respective pump and Stokes optical paths OPP and OPS. Respective pulse pickers in the respective optical paths choose select pump and Stokes pulses, which then propagate though respective pulse shapers I and II arranged in the respective optical paths. The pulse shapers impart the necessary time-dependent phases to the pulses to create chirped pump and Stokes pulses. An additional adjustable time delay line TDL in one of the optical paths may be used to make sure there is complete overlap between the pump and Stokes pulses in time domain.

The prepared pump and Stokes chirped pulses PP and PS propagate through respective optical fiber sections FP and FS. Objective lenses OLP and OPS in the pump and Stokes optical paths, respectively, are used to create a common focal spot on the sample. In a preferred embodiment, the objective lens OLP for the pump pulses is adapted so that the angle $\theta_L$ between them is adjustable, as shown.

A dichroic mirror DM is used to redirect the Stokes pulse PS toward the sample, as shown in FIG. 5. A signal SS generated in the sample is collected in the direction defined by the phase matching condition, shown in FIG. 5 as the Z-direction. A blocking filter is placed in front of a detector/processor unit (which n example embodiments comprises a CCD camera or a spectrometer) to remove residual light so that the sample signal can be cleanly detected and processed by the detector/processor unit. Note that the sample is placed on a scanning stage that is moveable in X, Y, Z to create an image of the sample using a camera or other image recording device in the detector/processing unit. A synchronizer unit is operably coupled to the pump and Stokes laser sources to control and synchronize the generation of the pump and Stokes light pulses PP and PS.

Pump and Stokes pathways (optical paths) are interchangeable. In an example embodiment, time delay line(s) TDL is/are placed in one or both optical paths OPP and OPS. It may be preferred in some cases to move the pump and Stokes objective lenses while keeping the sample stationary to obtain the sample image.

An example embodiment of the present invention uses a delayed probe pulse with respect to the pump and Stokes pulses used to create maximum coherence. This arrangement avoids (or reduces) the off-resonant background signal that can be generated in the CARS apparatus if pump, Stokes and probe pulses overlap in time.

Apparatus 10 can be used to perform both CARS microscopy and CARS spectroscopy. In the latter case, the detector/processor comprises a spectrometer. Tuning the pump-Stokes frequency difference is used to scan over possible transition frequencies in a sample.

Figure 6:
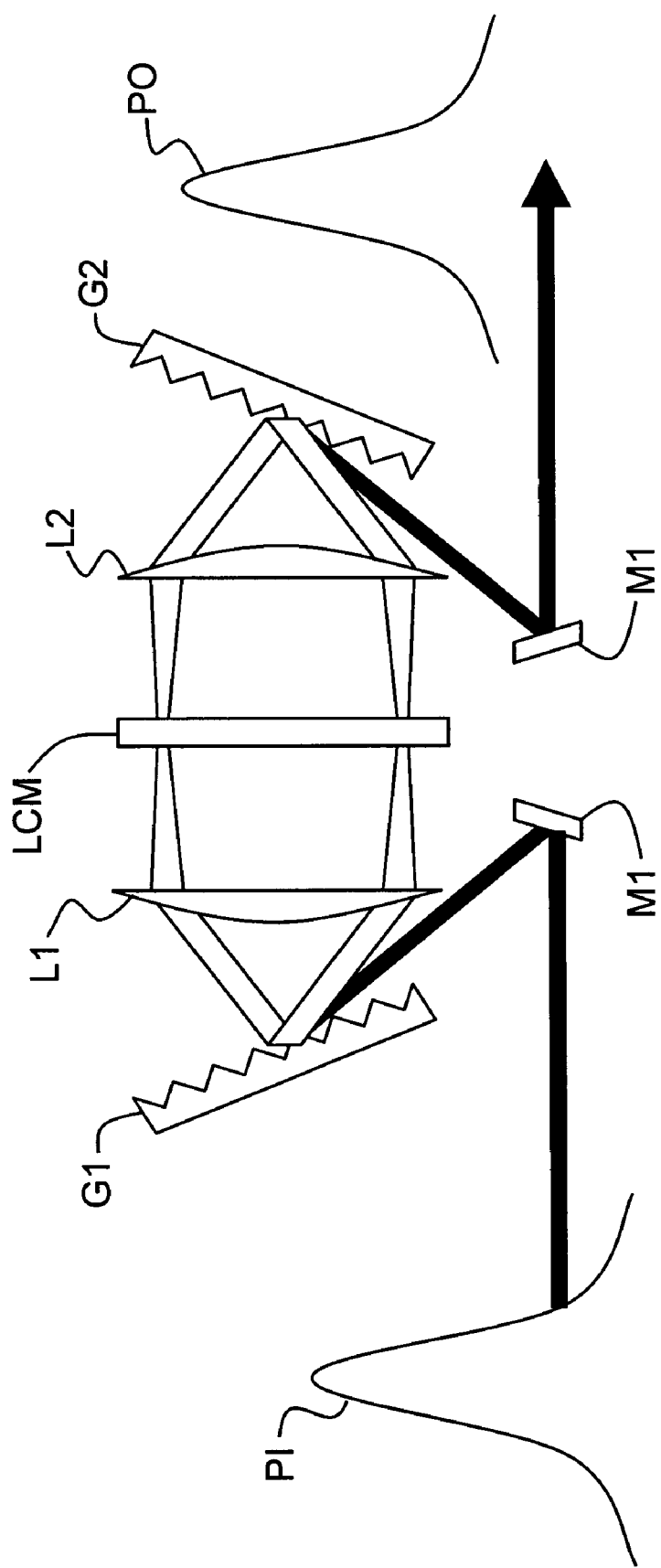
FIG. 6 is a schematic diagram of an example embodiment of a pulse shaper used to form the chirped pulses the apparatus of FIG. 5 and that employs a liquid crystal modulator (LCM)
Figure 7:
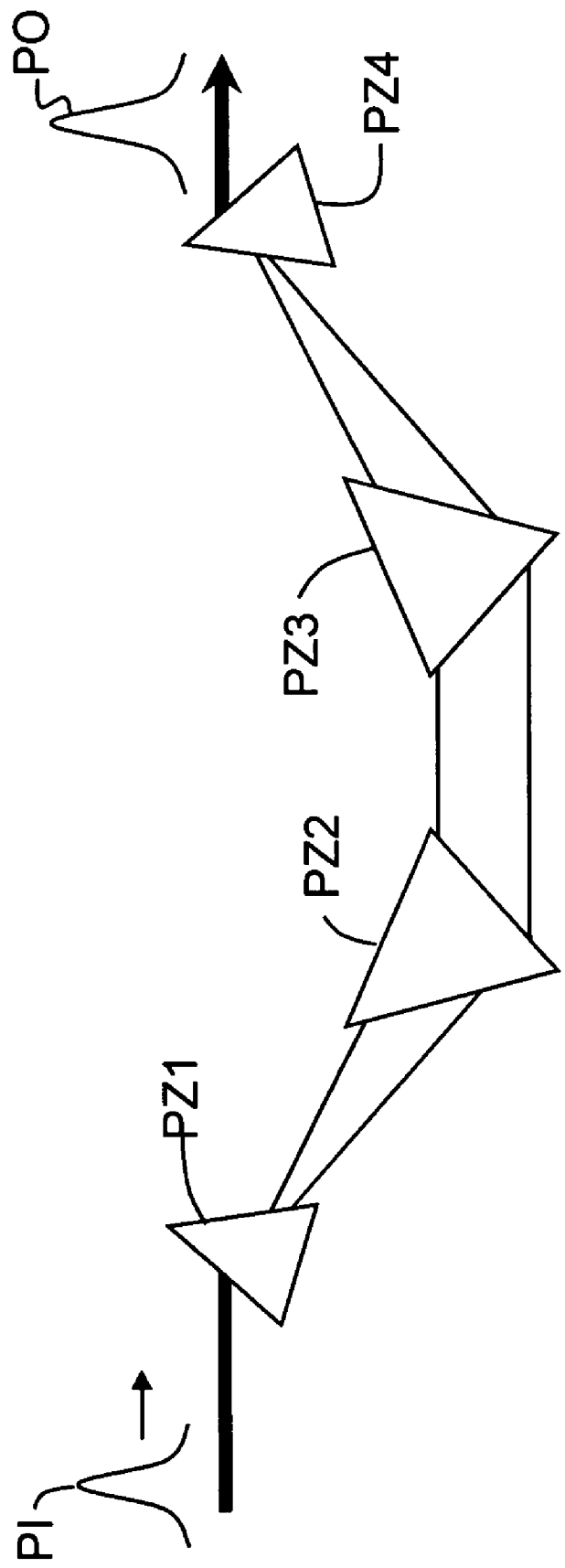
FIG. 7 is a schematic diagram of another example embodiment of a pulse shaper used to form the chirped pulses in the apparatus of FIG. 5 and that employs a number of prisms.

A schematic diagram of an example embodiment of a pulse shaper used in apparatus 10 of FIG. 5 is shown in FIG. 6. A chirp is applied to a transform-limited input pulse P1 by using two gratings G1 and G2, and two lenses L1 and L2, and controlling the voltage applied to each pixel in a liquid-crystal mask or modulator LCM as the dispersive element to produce the shaped output pulse. Select amounts of dispersion are imparted to select frequency components of the pulse. Fold mirrors M1 and M2 are used to form the grazing-incidence angles with gratings G1 and G2, respectively. A linear chirped (positive or negative) output pulse can also be obtained using four prisms PZ1 through PZ4 arranged in the pulse-shaper geometry shown in the example embodiment of FIG. 7.

Figure 8:
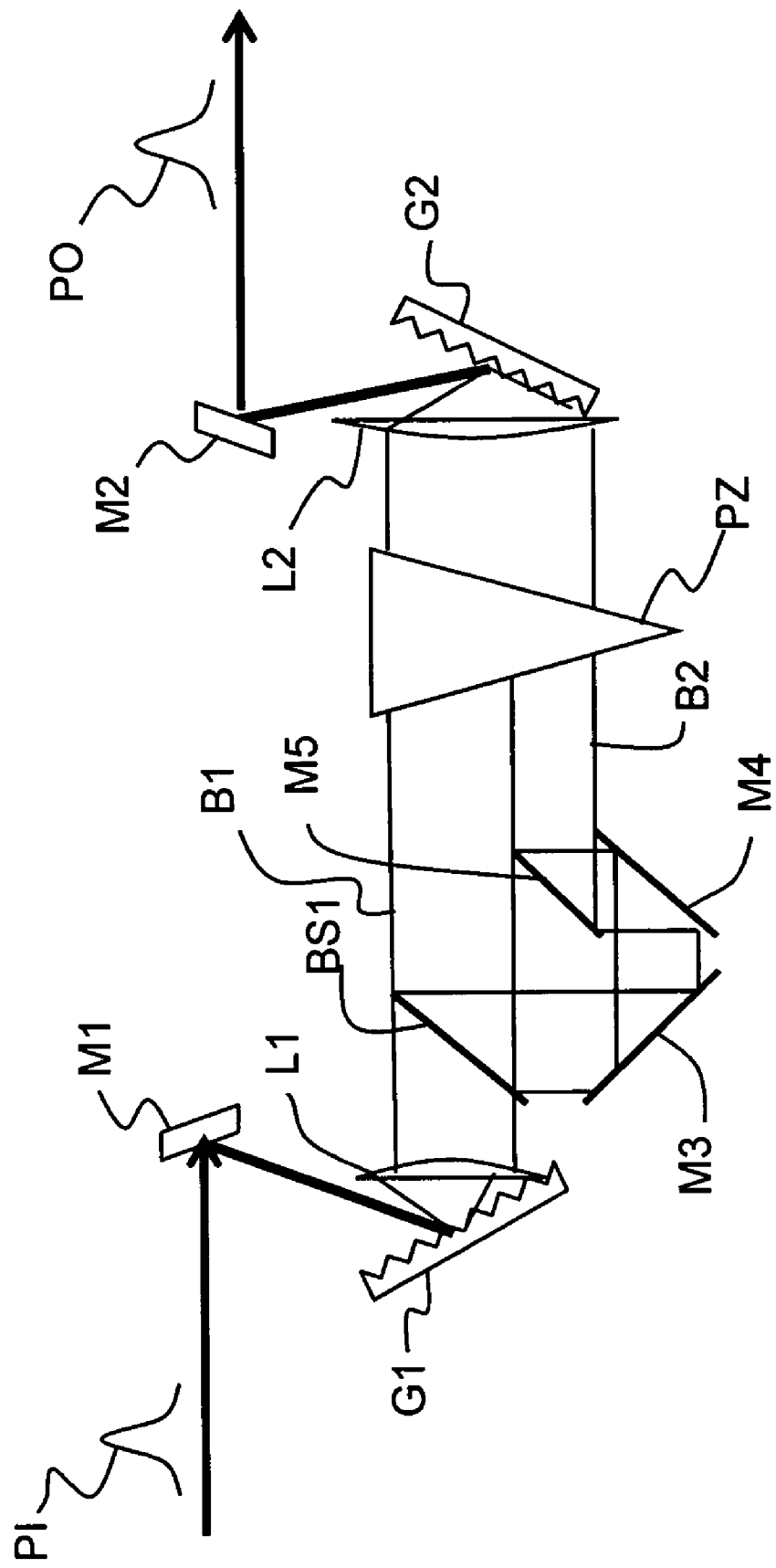
FIG. 8 is a schematic diagram of another example embodiment of a pulse shaper used for form chirped pulses in the apparatus of FIG. 5 and that employs a number of prisms to form a "roof-type" chirped pulse.

FIG. 8 illustrates an example embodiment of a pulse shaper used to form a roof-chirped output pulse. The input (transform-limited) pulse P1 passes through grating G1 and splits at the beam splitter BS1 into two beams B2 and B2. The spatial frequency chirp in one arm is reversed using three mirrors M1 through M3. Then beams B1 and B2 are recombined via mirror M3, yielding, for example, a blue-red-blue spatial chirp. A roof chirp is created using the dispersion of light. In the final step, grating G2 is used to convert the spatial chirp into the time domain. Lens L1 is used to collect the light diffracted by grating G1, and lens L2 is used to focus the diffracted light onto grating G2 to product output pulse PO.

Figure 9:
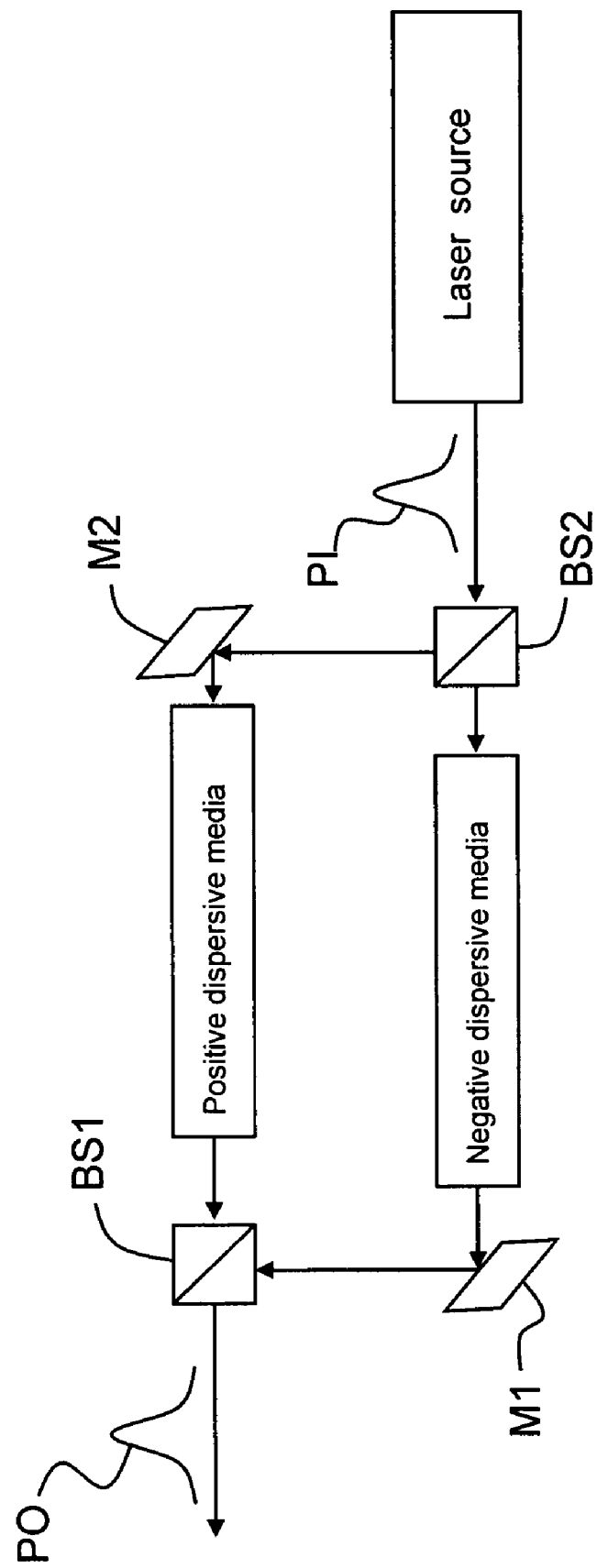
FIG. 9 is a schematic diagram of a generalized roof-pulse shaper.

FIG. 9 shows a schematic diagram of an example embodiment of a generalized roof-pulse shaper according to the present invention. The general idea of the roof-pulse shaper of FIG. 9 is to apply a positive chirp to one part of the split beam and a negative chirp to the other part of the split beam before recombining the two beams at a second beam splitter. Various materials with suitable dispersion (positive and negative) can be used in the pulse shaper. In an example embodiment, one or two additional time delay lines TDL (not shown) can be placed in one or both arms of the pulse-shaper.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

What is claimed is:

1. A method of performing imaging or spectroscopic analysis of a sample that contains one or more molecules using coherent anti-Stokes Raman scattering (CARS), comprising:
   generating Stokes light pulses along a first light path and pump light pulses along a second optical path;
   selecting and shaping select Stokes light pulses and pump light pulses to form temporally overlapping chirped Stokes and pump light pulses, including imparting a roof-pulse shape to either the Stokes light pulses or the pump light pulses;
   directing the chirped Stokes and pump light pulses to a select one of the at least one molecules so as to adiabatically excite a resonant mode of the select one molecule while leaving off-resonant modes unperturbed, thereby generating a sample signal in a direction defined by a phase-matching condition; and
   receiving and analyzing the sample signal.

2. The method of claim 1, including performing spectroscopy on the sample signal.

3. The method of claim 1, including performing imaging using the sample signal.

4. The method of claim 1, wherein the Stokes and pump light pulses have sufficiently high intensity to provide enough power to the select molecule to maintain Rabi frequencies necessary for adiabatic evolution of rovibrational states of the select molecule.

5. The method of claim 1, further comprising shaping the select Stokes and pump light pulses using first and second pulse shapers arranged in the first and second optical paths, respectively, wherein each pulse shaper includes a dispersive medium.

6. The method of claim 1, further comprising forming the Stokes and pump light pulses from first and second lasers operably coupled to and controlled by a synchronizer unit configured to synchronize the Stokes and pump light pulses.

7. The method of claim 6, wherein the dispersive element comprises a liquid crystal modulator.

8. The method of claim 1, further comprising directing the chirped Stokes and pump light pulses to the select molecule using first and second objective lenses.

9. The method of claim 8, wherein the dispersive element comprises a prism.

10. The method of claim 1, further comprising forming the chirped Stokes and pump light pulses by dispersing each of the light pulses by a diffraction grating and then providing the dispersed light pulses to a dispersive element configured to impart select amounts of dispersion to select light pulse frequencies.

11. An apparatus for performing coherent anti-Stokes Raman scattering (CARS), comprising:
   a sample having at least one molecule;
   a Stokes laser configured to generate Stokes light pulses and a pump laser configured to generate pump light pulses;
   means for forming overlapping, chirped Stokes and pump light pulses from the Stokes and pump light pulses, including imparting a roof-pulse shape to either the Stokes light pulses or the pump light pulses;
   optical means for directing the overlapping, chirped Stokes and pump light pulses to a select one of the at least one molecules so as to adiabatically excite a resonant mode of the select molecule while leaving off-resonant modes unperturbed so as to generate a sample signal defined by a phase-matching condition; and
   a detector/processor unit configured to receive and analyze the sample signal.

12. The apparatus of claim 11, further comprising a synchronizer unit operably coupled to the Stokes and pump lasers and configured to control the generation and synchronization of the Stokes and pump light pulses.

13. The apparatus of claim 11, wherein the sample comprises biological tissue.

14. The apparatus of claim 11, wherein the detector/processor unit includes at least one of an imaging unit and a spectrometer.

15. An apparatus for performing coherent anti-Stokes Raman scattering (CARS) to analyze a sample containing at least one molecule having a target resonant mode, comprising:

a sample holder configured to support the sample;

first and second synchronized lasers configured to generate initial Stokes and pump light pulses along respective first and second optical paths;

first and second pulse pickers respectively arranged along the first and second optical paths and respectively configured to transmit select ones of the Stokes and pump light pulses;

first and second pulse shapers respectively arranged along the first and second optical paths and respectively configured to impart either a positive or negative chirp to said select ones of the Stokes and pump light pulses from the respective first and second pulse pickers, and to impart a roof-pulse shape to either the Stokes light pulses or the pump light pulses;

first and second objective lenses respectively arranged along the first and second optical paths and respectively configured to receive the chirped Stokes and pump light pulses and direct said light pulses to a select one of the at least one molecule so as to adiabatically excite the target resonant mode while leaving off-resonant modes unperturbed so as to generate a sample signal in a direction defined by a phase-matching condition; and a detector/processor unit configured to receive and process the sample signal.

16. The apparatus of claim 15, wherein at least one of the first and second pulse shapers comprises first and second diffraction gratings and a dispersive element.

17. The apparatus of claim 15, wherein the dispersive element comprises one of a prism and a liquid crystal modulator.

18. The apparatus of claim 15, wherein the initial Stokes and pump light pulses are transform limited, and wherein said first and second pulse shapers are configured to stretch the initial transform-limited Stokes and pump light pulses via chirping by about 10 times or greater.

* * * * *